United States Patent
Weitkamp

(10) Patent No.: US 10,039,590 B2
(45) Date of Patent: Aug. 7, 2018

(54) CONNECTOR HAVING AN ALIGNMENT ELEMENT FOR FIXING THE ARMS OF A FORCEP

(71) Applicant: Sutter Medizintechnik GmbH, Freiburg (DE)

(72) Inventor: Dirk Weitkamp, Waldkirch (DE)

(73) Assignee: Sutter Medizintechnik GmbH, Freiburg (DE)

( * ) Notice: Subject to any disclaimer, the term of this patent is extended or adjusted under 35 U.S.C. 154(b) by 0 days.

(21) Appl. No.: 15/373,787

(22) Filed: Dec. 9, 2016

(65) Prior Publication Data

US 2018/0161089 A1  Jun. 14, 2018

(51) Int. Cl.
*H01R 13/64* (2006.01)
*A61B 18/14* (2006.01)
*A61B 18/00* (2006.01)
*A61B 17/00* (2006.01)

(52) U.S. Cl.
CPC ............. *A61B 18/1442* (2013.01); *A61B 2017/00526* (2013.01); *A61B 2017/00862* (2013.01); *A61B 2017/00955* (2013.01); *A61B 2018/00178* (2013.01)

(58) Field of Classification Search
CPC . H01R 2201/12; Y10S 439/909; H01E 13/64; A61B 18/1442

USPC ................................................ 439/909, 680
See application file for complete search history.

(56) References Cited

U.S. PATENT DOCUMENTS

| | | | |
|---|---|---|---|
| 8,108,994 B2 * | 2/2012 | Ariola, Jr. .......... | A61B 18/1442 29/854 |
| 2007/0106295 A1 * | 5/2007 | Garrison ............ | A61B 18/1445 606/50 |
| 2007/0173814 A1 * | 7/2007 | Hixson ............... | A61B 18/1445 606/51 |
| 2008/0103499 A1 * | 5/2008 | Sutter .................... | A61B 17/30 606/51 |
| 2009/0012519 A1 * | 1/2009 | Manrique ........... | A61B 18/1442 606/51 |
| 2011/0238066 A1 * | 9/2011 | Olson .................. | A61B 17/295 606/51 |

* cited by examiner

*Primary Examiner* — Chandrika Prasad
(74) *Attorney, Agent, or Firm* — Budzyn IP Law, LLC

(57) ABSTRACT

The present invention relates to a connector (1), a medical instrument and a method for manufacturing a medical instrument (2) according to the present invention. The connector comprises an alignment element (4) for receiving an end portion of at least one of the arms (3) of the instrument (2), thereby to align the arm (3) or arms (3) relative to the alignment element (4); and a housing element (7), in particular a bushing element, for receiving and holding the alignment element (4), wherein the alignment element (4) is insertable into the housing element (7). The medical instrument (2) comprises a connector (1) according to the present invention.

16 Claims, 2 Drawing Sheets

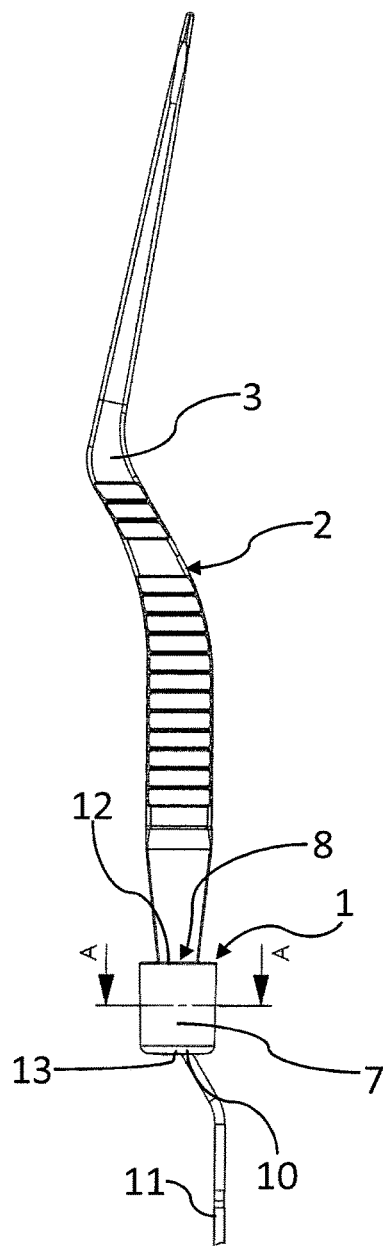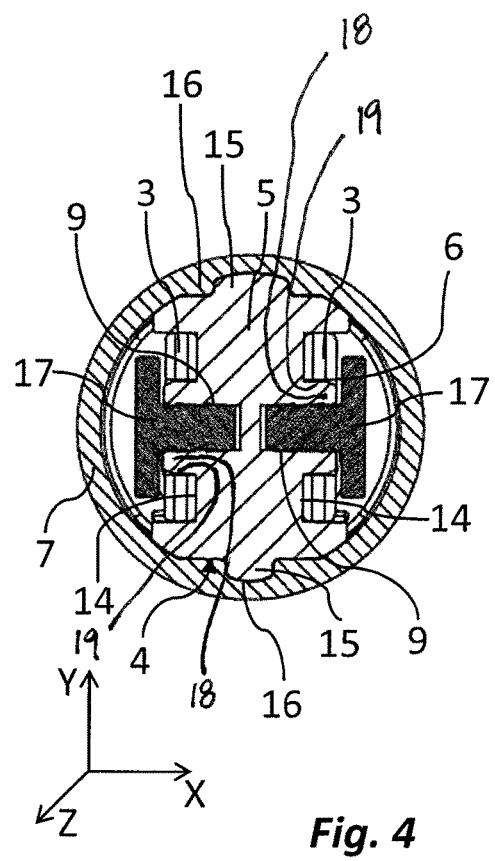
Fig. 3
Fig. 4

CONNECTOR HAVING AN ALIGNMENT ELEMENT FOR FIXING THE ARMS OF A FORCEP

TECHNICAL FIELD

The present invention relates to a connector, a medical instrument and a method for manufacturing a medical instrument.

BACKGROUND OF THE INVENTION

Connectors for medical instruments, in particular bipolar electrodes or forceps, are known. Such connectors are used for the assembly of forceps, wherein the arms of the forceps are paired by putting the arms into a housing element of the connector, which is formed as a hollow body. After placing the arms in the housing element, the end portions of the arms are fixed within the housing element, with the result that the arms are held together by the housing element. Usually a bonding agent is added into the housing element after the arms of the forceps are placed into the housing element. By the fixation of the arms within the housing element, a fulcrum point of the forceps is created.

However, a problem of such known connectors emerges during the assembly, when the arms of the medical instrument are to be fixed in the housing element. During this step the arms need to be stably aligned in relation to the housing element, especially during the curing time of the bonding agent. To achieve this, fabrication machines may be needed, which are able to hold the arms during the curing and to align the arms relative to the housing element.

If the arms are not constantly aligned relative to the housing element during the curing, they may shift from their intended position, which impairs the quality of the produced medical instrument. In particular, an incorrect or inaccurate arrangement of the arms leads to an instrument which is not suitable for use in medical treatments.

The present invention aims to address these problems and to provide a connector for a medical instrument, in particular a bipolar electrode or forceps, that enables an improved, especially more accurate, assembly of the medical instrument.

SUMMARY OF THE INVENTION

The connector according to the invention is characterized by the features according to claim 1. In particular the connector comprises:

- at least one alignment element for receiving an end portion of at least one of the arms of the instrument, thereby to align the arm or arms relative to the alignment element; and
- a housing element, in particular a bushing element, for receiving and holding the alignment element, wherein the alignment element is insertable into the housing element.

Accordingly, the connector of the invention addresses the problem of the alignment of the arm or arms of the medical instrument by providing an alignment element. The end portion/s of the arm or arms are received and held by the alignment element already before the alignment element is inserted into the housing element. In an embodiment the housing element may provide means for guiding the alignment element when the alignment element is inserted into the housing element. In such embodiment, the arm or arms are aligned relative to the housing element, in particular without the requirement of additional stabilization of the arm or arms in its/their position by further technical devices.

The connector may be implemented as a socket comprising the at least one alignment element and the housing element.

In an embodiment the alignment element of the connector is arranged to align the arm or arms relative to the alignment element in at least two different directions. In particular, the alignment element is arranged to align the arm or arms relative to the alignment element in X- and Y-directions. Preferably, the alignment element is arranged to align the arm or arms relative to the alignment element in X-, Y- and Z-directions (see FIG. 4). The alignment element may be held within the housing element by friction. In particular, in a preferred embodiment, the alignment element is insertable into a chamber of the housing element until it reaches a final position, in which position the friction between the alignment element and the housing element is strongest. For example, the alignment element has the shape of a wedge, which is insertable with its smaller end into the chamber of the housing element.

In an embodiment the arm or arms is/are aligned relative to the alignment element before the alignment element is inserted into the housing element. This allows bringing the arm or arms in a stable position relative to the alignment element before inserting the alignment element together with the end portion of the arm or arms into the housing element.

In an embodiment the alignment element has a septum and/or forms a septum within a chamber of the housing element when inserted into the housing element. Preferably of the side edges of the septum are in contact with the inside wall of the housing element, when the alignment element is inserted into the housing element. The septum defines two portions within the chamber, in particular equally sized portions, one for each arm.

According to another embodiment, the housing element comprises an electrical connection for supplying electric current to the arm or arms of the instrument. Thus, the electric current can be applied for medical treatments.

In another embodiment the alignment element has at least one guiding element, in particular one or more peripheral projections, and the housing element has at least one complementary reception element, in particular one or more recesses located on an inside wall of the housing element, for receiving the guiding element when the alignment element is inserted into the housing element. Preferably, the at least one guiding element and the at least one reception element are formed such that the guiding element is insertable into the receiving element only in one direction. Accordingly, with this configuration it can be prevented that the alignment element is incorrectly inserted into the housing element.

In another embodiment, the alignment element comprises two mounting portions on opposing sides of the alignment element for fixing the end portions of the arms to the alignment element. Especially, each mounting element is for fixing one end portion. Thus, each mounting portion defines a part of the alignment element for receiving and holding an arm. In particular, the mounting portions are shaped such that they define a definite position in which each arm of the medical instrument can be arranged.

According to one embodiment, the connector further comprises a fastening means for fastening the arm or arms to the alignment element. This further stabilizes the alignment of the arm or arms. Preferably the fastening means comprises an aperture or apertures, especially on opposing sides of the alignment element. There may also be a fastening pin or fastening pins insertable into an aperture or apertures in the fastening means and/or the alignment element.

In one embodiment, the housing element and/or the alignment element is/are made from an electrically insulating material.

In one embodiment, the housing element has the shape of a cylinder or a conic section, wherein one of the bases of the cylinder or the conic section forms an opening through which the alignment element is insertable into the housing element, and/or the opposing base is closed except for at least one through hole for one or more electric lines for connecting an external power supply to the arm or arms of the medical instrument. The electric lines comprise one or more electric cables and/or one or more pins to form a plug for connecting with an external electrical power supply.

In another embodiment the alignment element, when inserted in the housing element, is interlocked and/or friction-locked within an inner chamber of the housing element. Thus, the alignment element is fixed within the housing element without the requirement of a bonding agent, like a glue or resin.

In one embodiment the housing element comprises a stop element defining an end position of the alignment element when fully inserted into the housing element. When the alignment element impinges on the stop element the end position is reached.

In another embodiment the alignment element comprises a latch device whereby the alignment element is latched in position when fully inserted in the housing element.

According to another embodiment the closed base of the housing element comprises a sealing element, wherein the at least one through hole is arranged in the sealing element. Preferably, the sealing element is made from a thermoplastic elastomer. The sealing element prevents liquid from entering the housing element through the at least one through hole, since liquid could impair the function of the medical instrument. In addition, the sealing element prevents glue or resin to leak out from the housing element before the glue or resin is fully cured.

Further, the present invention provides a medical instrument, in particular a bipolar electrode or a forceps, comprising a connector as described herein.

Moreover, the present invention also provides a method for manufacturing a medical instrument, in particular a bipolar electrode or a forceps, comprising the steps:
- providing a connector, preferably as described herein;
- fixing an end portion of an arm or arms of the medical instrument to an alignment element, thereby aligning the arm or arms relative to the alignment element;
- placing the alignment element and the end portion of the arm or arms into a chamber of a housing element until an end position of the alignment element and the arm or arms is reached within the chamber;
- fixing the alignment element and the inserted end portion of the arm or arms in the end position.

The method according to the invention makes it feasible to manufacture a medical instrument solving the problem that the arm or arms have to be aligned correctly before they are fixed within the housing element by using a connector as described above. Hence, the above described advantages pertain also to the method according the invention.

In one embodiment the fixing of the alignment element and the inserted end portion/s of the arm or arms in the end position is performed by adding a bonding agent, preferably a glue and/or a resin, into the chamber of the housing element and curing the bonding agent and/or by using a mechanical fastening system, in particular a mechanical fastening system as described above, e.g. a latch. Preferably, the alignment element is interlocked and/or friction-locked within an inner chamber of the housing element.

In another embodiment the arm or arms of the medical instrument are connected to an electric line, in particular by inserting at least one cable and/or at least one pin through a through hole of the housing element before fixing the alignment element within the housing element.

BRIEF DESCRIPTION OF THE DRAWINGS

The present invention may be better understood from the following description of non-limiting embodiments, with reference to the attached drawings, wherein:

FIG. 3 schematically shows a top view of the medical instrument of FIG. 2; and

FIG. 4 shows a cross section along line A-A in FIG. 3.

DETAILED DESCRIPTION OF EXEMPLARY EMBODIMENTS

Figure 1:
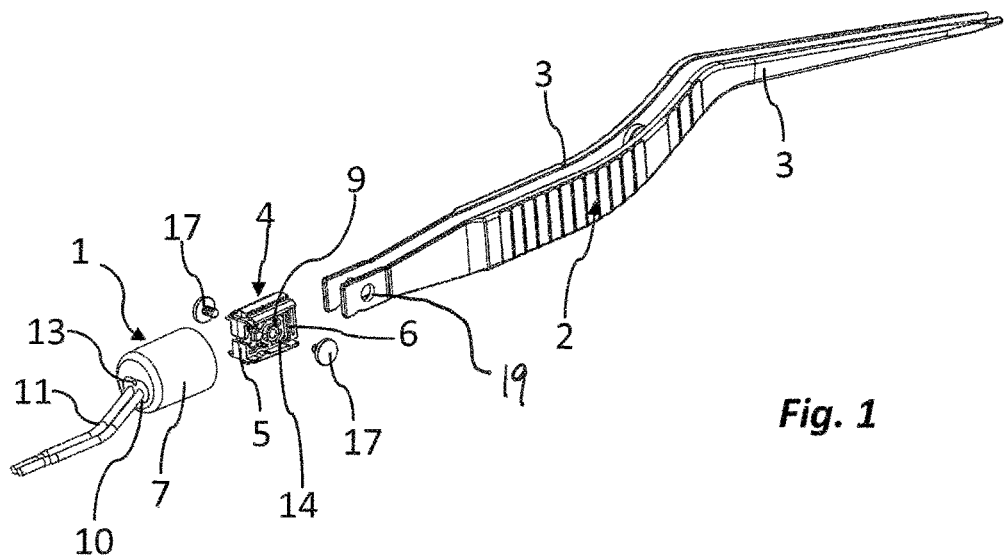
FIG. 1 schematically shows an exploded view of a connector in accordance with an embodiment of the present invention, and components of a medical instrument in accordance with an embodiment of the present invention.
Figure 2:
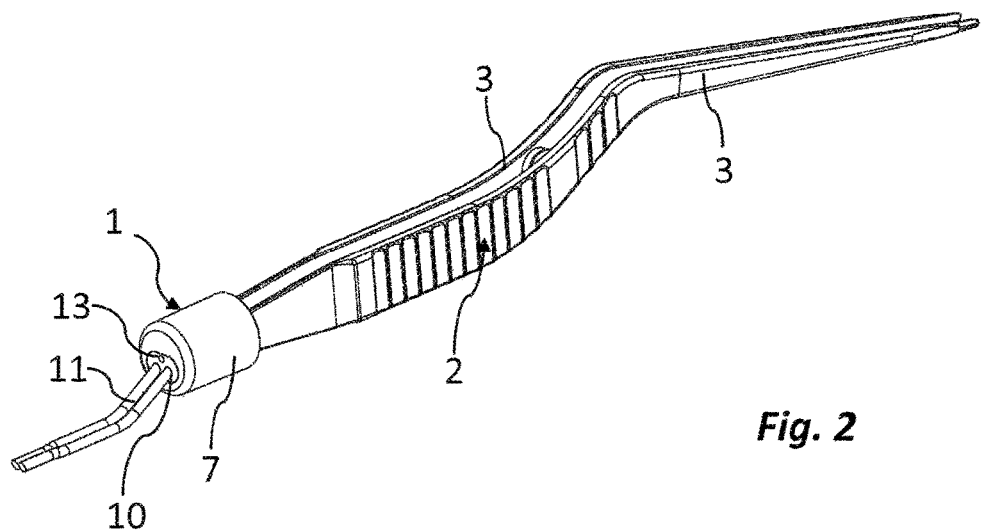
FIG. 2 schematically shows a medical instrument comprising the connector in accordance with an embodiment of the present invention in an assembled state comprising a connector according to an embodiment of the invention.

FIG. 1 schematically shows an exploded view of a connector 1 in accordance with an embodiment of the present invention and components of a medical instrument 2 in accordance with an embodiment of the present invention. In particular, the connector 1 is usable for manufacturing a medical instrument 2, such as a bipolar electrode and/or forceps. In the illustrated embodiment, the medical instrument 2 is a forceps that has two arms 3 which are connected with each other in an assembled state, as shown in FIGS. 2 and 3. The connector 1 comprises an alignment element 4 and a housing element 7. The housing element 7 can be formed as a bushing element having a round cross-section, as shown in FIG. 1. It may also have a rectangular, hexagonal or any other suitable cross-section. The housing element 7 forms an inner chamber for receiving the alignment element 4.

The alignment element 4 comprises two mounting portions 14 on opposing sides of the alignment element 4 for fixing the end portions of the arms 3 to the alignment element 4. Thereby, the arms 3 are fixed, so as to be in fixed alignment, to the alignment element 4. In particular, the arms 3 are aligned relative to the alignment element 4 even before the alignment element 4 is inserted into the housing element 7. The mounting portions 14 may each include a protruding post 18 formed to be insertingly received in a through-aperture 19 of the arms 3, as shown in FIG. 4.

The connector 1 further comprises fastening means 6 for fastening end portions of the arms 3 to the alignment element 4. As shown in FIGS. 1-4, the fastening means may comprise apertures 9 on opposing sides of the alignment element 4 and two fastening pins 17, which are insertable into the apertures 9 for fixing the end portions of the arms 3 to the alignment element, thereby aligning the arms 3 relative to the aligning element 4. The apertures 9 may be defined in the protruding posts 18.

The housing element 7 is arranged for receiving and holding the alignment element 4. The housing element 7 comprises an opening 12, which leads to the inner chamber of the housing element 7. The alignment element 4 is insertable into the housing element 7 through the opening 12, thereby aligning the arms 3 relative to the housing element 7. The housing element 7 is formed as a conic section or a cylinder, wherein one base of the body of the housing element 7 is open and the opposite base is closed. As indicated above, the housing element 7 may also have a rectangular, hexagonal or any other suitable cross-section.

In FIGS. 2 and 3 the medical instrument 2 is shown in an assembled configuration. The alignment element 4 is inserted into the housing element 7, whereby the arms 3 are aligned relative to the alignment element 4 and the housing element 7 in X- and Y-directions, preferably in X-, Y- and Z-directions. In the assembled state a fulcrum point 8 of the medical instrument 2 is created by the connector 1.

The alignment element 4 comprises at least one guiding element 15 and the housing element 7 has at least one complementary reception element 16. Thus, the housing element 7 provides a guide for inserting the alignment element 4 into the inner chamber of the housing element 7. As shown in FIG. 4, the guiding element is formed as one or more peripheral projections and the reception element 16 is formed as one or more recesses, which are located on an inside wall of the housing element 7. The reception element 16 is arranged for receiving the guiding element 15 when the alignment element 4 is inserted into the housing element 7. Preferably the at least one guiding element 15 and the at least one reception element 16 are formed such that the guiding element 15 is insertable into the reception element 16 only in one direction.

In the assembled state of the medical instrument 2, the alignment element 4 forms a septum 5 within the inner chamber of the housing element 7, hence, when it is inserted into the housing element 7. Thereby, the septum 5 is located to separate the inner chamber into two equally sized parts, wherein in each part, one arm 3 is fixed to the septum 5.

The housing element 7 comprises an electrical connection for supplying electric current to the arms 3 of the instrument 2. One side of the housing element 7 comprises openings. The openings may be arranged in a sealing element 13, which prevents liquid from entering the inside of the housing element 7. In addition, the sealing element 13 prevents glue or resin to leak out from the housing element 7 before the glue or resin is fully cured. The sealing element 13 comprises a through hole 10 for one or more electric lines 11. The electric lines are arranged for connecting an external power supply to the arms 3 of the medical instrument 2. Preferably, the sealing element 13 is made from a thermoplastic elastomer. As shown in FIGS. 1-3, the electric line or lines 11 may comprise electric cables. Alternatively or additionally the electric lines 11 may comprise one or more pins to form a plug for connecting with an external electrical power supply.

The housing element 7 and the alignment element 4 may comprise a latch device. When the alignment element is inserted, in particular fully inserted, into the housing element 7, the alignment element 4 is latched in position.

Therefore, the alignment element 4 and the arms 3 can be fixed within the housing element 7 with or without a bonding agent. Furthermore, a combination of a mechanical fixation with an additional fixation by a bonding agent is also possible.

| Reference signs | |
|---|---|
| 1 | connector |
| 2 | medical instrument |
| 3 | arm |
| 4 | alignment element |
| 5 | septum |
| 6 | fastening means |
| 7 | housing element |
| 8 | fulcrum point |
| 9 | aperture |
| 10 | through hole |
| 11 | electric line |
| 12 | opening |
| 13 | sealing element |
| 14 | mounting portion |
| 15 | guiding element |
| 16 | reception element |
| 17 | fastening pin |

The invention claimed is:

1. A connector (1) for a bipolar electrode or forceps, the bipolar electrode or forceps having first and second arms (3), the connector (1) comprising:
   at least one alignment element (4) for receiving end portions of the first and second arms (3) so as to fix the first and second arms (3) to the alignment element (4) with the first and second arms (3) being in fixed alignment relative to the alignment element (4); and
   a housing element (7) for receiving and holding the alignment element (4), wherein the alignment element (4) is insertable into the housing element (7) with the first and second arms (3) being fixed to the alignment element (4).

2. The connector (1) of claim 1, wherein the alignment element (4) has a septum (5).

3. The connector (1) of claim 1, wherein the housing element (7) comprises an electrical connection for supplying electric current to the first arm (3).

4. The connector (1) of claim 1, wherein the alignment element (4) has at least one guiding element (15) and the housing element (7) has at least one complementary reception element (16) for receiving the guiding element (15) when the alignment element (4) is inserted into the housing element (7).

5. The connector (1) of claim 1, wherein the alignment element (4) further comprises two mounting portions (14) on opposing sides of the alignment element (4) for holding the end portions of the first and second arms (3) in fixed alignment relative to the alignment element (4).

6. The connector (1) of claim 1, further comprising fastening means (6) for fastening the first arm (3) to the alignment element (4), wherein the fastening means (6) comprises an aperture (9) and a fastening pin (17) insertable into the aperture (9).

7. The connector (1) of claim 1, wherein the alignment element (4) is made from an electrically insulating material.

8. The connector (1) of claim 1, wherein the housing element (7) has the shape of a cylinder with opposing bases, wherein one of the bases of the cylinder forms an opening (12) through which the alignment element (4) is insertable into the housing element (4), and the opposing base is closed and comprises at least one through hole (10) for one or more electric lines (11) for connecting an external power supply to the first and second arms (3), wherein the electric lines (11) comprise one or more electric cables and/or one or more pins to form a plug for connecting with an external electrical power supply.

9. The connector (1) of claim 1, wherein the alignment element (4), when inserted into the housing element (7), is interlocked and/or friction-locked within an inner chamber of the housing element (7).

10. The connector (1) of claim 8, wherein the closed base of the housing element (7) comprises a sealing element (13), and, wherein the at least one through hole (10) is arranged in the sealing element (13).

11. A bipolar electrode or a forceps having first and second arms (3), the bipolar electrode or forceps comprising a connector (1) according to claim 1.

12. The connector (1) of claim 4, wherein the at least one guiding element (15) and the at least one reception element (16) are formed such that the at least one guiding element (15) is insertable into the at least one reception element (16) in one direction.

13. The connector of claim 1, wherein the housing element (7) includes a stop element defining an end position of the alignment element (4) when fully inserted into the housing element (7).

14. The connector of claim 1, wherein one or both of the housing element (7) and the alignment element (4) includes a latch, and, wherein the alignment element (4) is latched to the housing element (7) when fully inserted into the housing element (7).

15. The connector of claim 10, wherein the sealing element (13) is made from a thermoplastic elastomer.

16. The connector of claim 5, wherein the first arm (3) having a through-aperture formed in the end portion thereof, and, wherein, the first mounting portion (14) having a protruding post formed to be insertingly received in the through-aperture of the first arm (3) to fix the end portion of the first arm (3) to the alignment element (4).

* * * * *